United States Patent
Hawkes et al.

(10) Patent No.: US 9,320,695 B2
(45) Date of Patent: Apr. 26, 2016

(54) HAIR TREATMENT METHODS

(71) Applicant: Perachem Limited, Leeds (GB)

(72) Inventors: Jamie Anthony Hawkes, Leeds (GB);
David Malcolm Lewis, Otley (GB);
John Mama, Leeds (GB)

(73) Assignee: Perachem Limited, Yeadon, Leeds (GB)

( * ) Notice: Subject to any disclaimer, the term of this patent is extended or adjusted under 35 U.S.C. 154(b) by 0 days.

(21) Appl. No.: 14/389,925

(22) PCT Filed: Mar. 22, 2013

(86) PCT No.: PCT/GB2013/050756
§ 371 (c)(1),
(2) Date: Oct. 1, 2014

(87) PCT Pub. No.: WO2013/150268
PCT Pub. Date: Oct. 10, 2013

(65) Prior Publication Data
US 2015/0047131 A1   Feb. 19, 2015

(30) Foreign Application Priority Data

Apr. 2, 2012   (GB) .................................. 1205900.2

(51) Int. Cl.
*A61Q 5/10* (2006.01)
*A61K 8/41* (2006.01)
*A61Q 5/06* (2006.01)
*A61K 8/46* (2006.01)

(52) U.S. Cl.
CPC ................... *A61K 8/416* (2013.01); *A61K 8/46* (2013.01);*A61Q 5/065* (2013.01); *A61Q 5/10* (2013.01); *A61K 2800/884* (2013.01);

(58) Field of Classification Search
CPC ........... A61Q 5/10; A61K 8/46; A61K 8/416; A61K 2800/884
USPC ....................................... 8/405; 132/202, 208
See application file for complete search history.

(56) References Cited

U.S. PATENT DOCUMENTS

| | | | |
|---|---|---|---|
| 3,396,736 A | 8/1968 | Shansky | |
| 3,399,682 A | 9/1968 | Isaji et al. | |
| 3,892,845 A | 7/1975 | Cunningham et al. | |

(Continued)

FOREIGN PATENT DOCUMENTS

| | | |
|---|---|---|
| DE | 100 55 947 A1 | 5/2002 |
| EP | 1 366 755 A1 | 12/2003 |

(Continued)

OTHER PUBLICATIONS

Search Report, GB 1305301.2, dated Aug. 6, 2013.
(Continued)

*Primary Examiner* — Eisa Elhilo
(74) *Attorney, Agent, or Firm* — HoustonHogle, LLP

(57) ABSTRACT

A method of treating a material, the method comprising the steps of: (i) contacting the material with a coloring composition comprising a dye compound; and (ii) contacting the material with a composition comprising a quaternary ammonium salt.

11 Claims, 1 Drawing Sheet

(56) References Cited

U.S. PATENT DOCUMENTS

Figure 1:
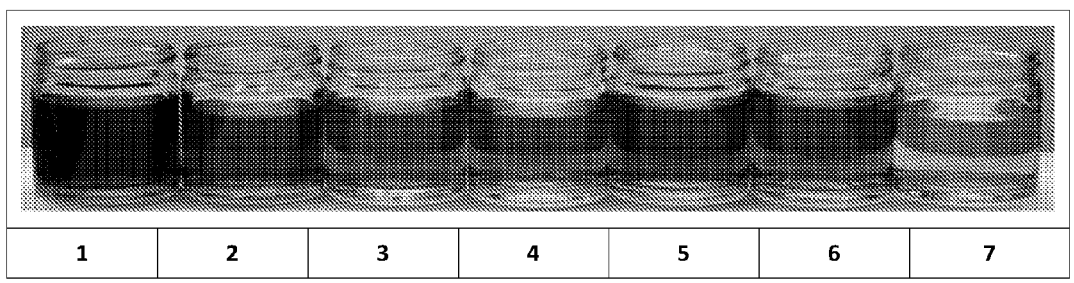

| | | | |
|---|---|---|---|
| 5,376,146 | A | 12/1994 | Casperson et al. |
| 6,379,657 | B1 | 4/2002 | Lorenz et al. |
| 6,398,822 | B1 | 6/2002 | Brock et al. |
| 7,413,579 | B2 * | 8/2008 | Seiler et al. .................. 8/405 |
| 7,972,388 | B2 * | 7/2011 | Hamilton et al. ............. 8/405 |
| 2004/0244126 | A1 | 12/2004 | Vena et al. |
| 2012/0141398 | A1 | 6/2012 | Chuang |
| 2015/0068548 | A1 | 3/2015 | Hawkes et al. |

FOREIGN PATENT DOCUMENTS

| | | |
|---|---|---|
| EP | 1 313 830 B1 | 7/2005 |
| EP | 2 382 962 A1 | 11/2011 |
| GB | 951021 | 3/1964 |
| GB | 1077758 | 8/1967 |
| WO | WO 03/074016 A1 | 9/2003 |
| WO | WO 2007/146672 A2 | 12/2007 |
| WO | WO 2009/009653 A2 | 1/2009 |
| WO | 2009112858 A2 | 9/2009 |
| WO | 2010032030 A2 | 3/2010 |
| WO | WO 2010/032034 A2 | 3/2010 |
| WO | WO 2010/097339 A2 | 9/2010 |
| WO | WO 2012/113724 A2 | 8/2012 |

OTHER PUBLICATIONS

Search Report, GB 1316255.7, dated Oct. 14, 2013.
Search Report, GB 1305313.7, dated May 14, 2013.
International Preliminary Report on Patentability, PCT/GB2013/050756, "Hair Treatment Methods," issued Oct. 7, 2014.
International Search Report, PCT/GB2013/050756, entitled "Hair Treatment Methods," mailed May 8, 2014.
Written Opinion of the International Searching Authority, PCT/GB2013/050756, entitled "Hair Treatment Methods," mailed May 8, 2014.
Zhou, Y., et al., "Protection of oxidative hair color fading from shampoo washing by hydrophobically modified cationic polymers," *J. Cosmet. Sci.*, 60:217-238 (2009).
Database GNPD [online, http://www.gnpd.com] Mintel: "Permanent Hair Colourant Cream," Accession No. 1380589 Sep. 2010.
Written Opinion, PCT/GB2013/050757, "Hair Treatment Methods," Dec. 6, 2013.
International Search Report, PCT/GB2013/050757, "Hair Treatment Methods," mailed Dec. 6, 2013.
International Preliminary Report on Patentability, PCT/GB2013/050757, "Hair Treatment Methods," Oct. 7, 2014.
U.S. Patent Office Action, U.S. Appl. No. 14/389,950, mailed Oct. 8, 2015.

* cited by examiner

HAIR TREATMENT METHODS

RELATED APPLICATIONS

This application is the U.S. National Stage of International Application No. PCT/GB2013/050756, filed Mar. 22, 2013, which designates the U.S., published in English, and claims priority under 35 U.S.C. §§119 or 365(c) to Great Britain Application No. 1205900.2 filed Apr. 2, 2012.

The present invention relates to methods for colouring materials, in particular colouring keratinous fibre materials, for example hair.

The colouring of human hair is a long-established practice in many cultures. There are many challenges for those working in the field of hair colouration. It is desirable to provide dyes and dyeing methods by which hair can be predictably coloured to consistently provide the desired shade. Hair colouring methods should be efficient in order to allow short contact times which provide wash durable and light durable colour and any damage to the hair should be kept to a minimum.

One problem with many existing hair colouring methods and compositions is that all of the colour is not sufficiently fixed onto the hair at the end of the dyeing process. "Bleeding" of the dye may occur and colour may rub off and stain materials which come into contact with the dyed hair, for example hats, bed linen, towels and collars of shirts and blouses.

It is an aim of the present invention to provide an improved hair colouring method having improved bleed resistance.

According to a first aspect of the present invention there is provided a method of treating a material, the method comprising the steps of:
(i) contacting the material with a colouring composition comprising a dye compound; and
(ii) contacting the material with a composition comprising a quaternary ammonium salt.

The method of the present invention may be used to treat any suitable material. Preferably it is used to treat keratin based material. Most preferably it is used to treat hair, especially human hair.

Step (i) comprises contacting the material with a composition comprising a dye compound. Any suitable dye compound may be selected.

In some embodiments the colouring composition may comprise a reactive dye.

As will be readily understood by the person skilled in the art of colour science, a reactive dye typically contains an electrophilic group that can be activated and allowed to directly react with a nucleophile in the material, forming a covalent bond. Reactive dye compounds may typically include a vinyl sulfone, an acrylamido or a halogenated triazine moiety, but the skilled person would be aware of dyes of other structures falling within this class.

In some embodiments the colouring composition may comprise a compound of formula (I)

$$D\text{-}L\text{-}CHQ\text{-}CH_2\text{—}SR \quad (I)$$

wherein D is a chromophore; L is a linking group selected from $SO_2$, NHCO, and $NHSO_2$; Q is a hydrogen or halogen atom; and R is selected from $C_1$-$C_4$ alkyl, $(CH_2)_n COOH$, $(CH_2)_n CONH_2$, $(CH_2)_n SO_3 H$, $(CH_2)_n COOM$, $(CH_2)_n PO_3 H$, $(CH_2)_n OH$, $(CH_2)_n SSO_3^-$, $(CH_2)_n NR^1{}_2$, $(CH_2)_n N^+R^1 H_2$, $(CH_2)_n NHCOR^1$, $PhSSO_3^-$, $PhSO_3 H$, $PhPO_3 H$, $PhNR^1{}_2$, $PhN^+R^1{}_3$, $(CH_2)_2 CH(SH)R^1(CH_2)_3 COOH$, and

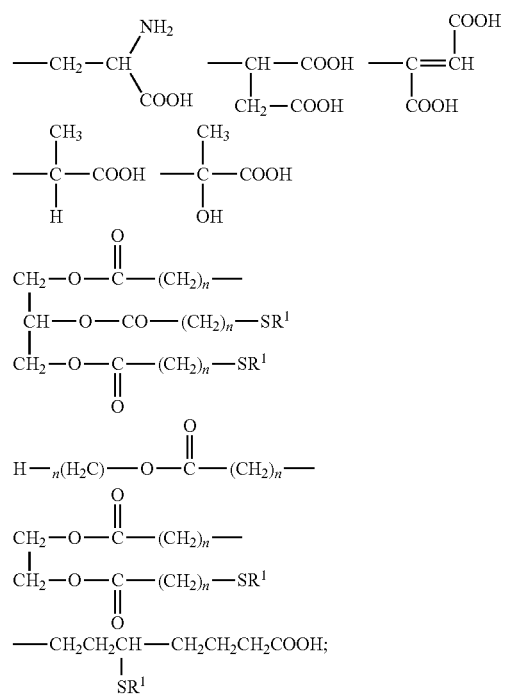

n is an integer in the range of 1 to 4 wherein within the same molecule each n is not necessarily the same integer; M is a cation of an alkaline earth metal, alkali metal, $NH_4^+$ or $NR^1{}_3{}^+$; and $R^1$ is $C_1$-$C_4$ alkyl.

Dye compounds of this type are further described in the applicant's granted U.S. Pat. No. 8,016,895.

In some embodiments the colouring composition may comprise a dye compound selected from the classes of direct dyes, basic dyes, acid levelling dyes, premetallised dyes (including 2:1 premetallised acid dyes and 1:1 premetallised acid dyes), acid milling dyes, food dyes, natural dyes, leather dyes, pigment dyes, sulphur dyes, solvent dyes, vat dyes, ingrain dyes, mordant dyes, fluorescent brightening agents and disperse dyes.

In some preferred embodiments the colouring dye is selected from the classes of direct dyes, acid levelling dyes, premetallised dyes (including 2:1 premetallised acid dyes and 1:1 premetallised acid dyes) and acid milling dyes. Also useful are water-solubilised vat dyes, for example those based on sulfate esters of hydroquinone-based dyes.

The skilled person would be familiar with the above-mentioned classes of dye and would understand the types of compounds which fall within each class.

Examples of suitable dyes falling within the above classes are described in the applicant's earlier application PCT/GB/2009/051162.

The colouring composition used in step (i) of the method of the present invention preferably comprises a water soluble dye compound containing sulfonate and/or carboxylate groups.

By this we mean that the dye compound includes at least one carboxylate group or at least one sulfonate group.

Such dye compounds may include more than one carboxylate group and/or more than one sulfonate groups.

By carboxylate group we mean to refer to the residue of a carboxylic acid, $—CO_2^-$. By sulfonate group we mean to refer to the residue of a sulfonic acid $—SO_3^-$.

The carboxylate and/or sulfonate groups may be present as the free acid i.e. —COON or —SO₃H. Preferably they are present as the salt of the acid i.e., —COO⁻M⁺ or —SO₃M⁺ where M⁺ is a cation. Suitable cations include ammonium or substituted ammonium cations, and alkali metal and alkaline earth metal cations. Preferred are alkali metal cations, for example sodium and potassium cations. Most preferably the carboxylate and/or sulfonate groups are present as their sodium salts.

The dye compounds used in step (i) of the method of the present invention also include a chromophore. Preferably the dye compound includes a chromophore that is active in the visible region of the electromagnetic spectrum. However dye molecules including a chromophore that is active in the ultraviolet or infrared region of the electromagnetic spectrum are also within the scope of the invention.

The dye compounds used in the colouring composition may include dye compounds generally known to those skilled in the art as acid dyes, including the classes of acid milling dyes and acid levelling dyes.

Acid dyes are typically water soluble anionic dyes that contain one or more sulphonic acid groups, usually as the sodium salt, carboxylic acid groups or hydroxyl groups (less common). The structure on which the dyes are based depends on the colour. Acid dyes can be based on a number of chromophores, which tend to dictate the colour of the dye. For example, blue acid dyes are often based on an anthraquinone moiety, or triphenylmethane, although some may be azo based, formazan or phthalocyanine based. Red, orange and yellow acid dyes tend to be based upon azo moieties.

Compounds based on stillbene or coumarin including carboxylate and/or sulfonate residues may be useful in compositions for providing special effects. Such compounds are known to be fluorescent.

In some preferred embodiments the dye compounds used in the colouring compositions do not include any transition metals.

In some preferred embodiments the dye compounds used in the colouring compositions do not include any chelated metal species.

The Colour Index International is a standard classification system for dyes and pigments which contains historic, proprietary, generic names and generic numbers that have been applied to colours. It was first published in 1924 and has been updated and reprinted since. The 2^(nd) (1956), P(1971) and 4^(th) (2002) editions are jointly published and maintained by the Society of Dyers and Colourists (SDC) (UK) and American Association of Textile Chemists and Colourists (AATCC). The structures of the dye compounds shown in this specification are taken from the Colour Index International.

Examples of suitable dyes for use in the colouring composition contacted with the material in step (i) of the method of the present invention include those of the following group, (1):

(A)
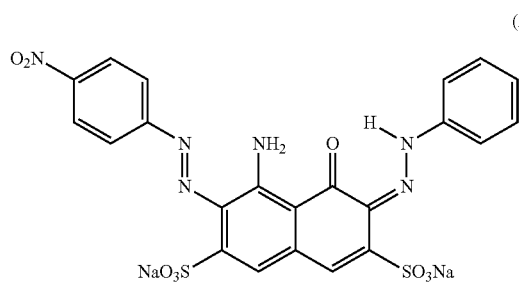

(B)
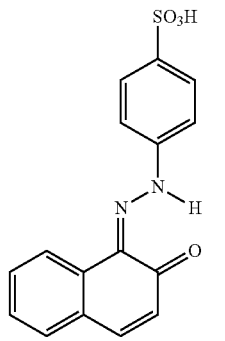

(C)
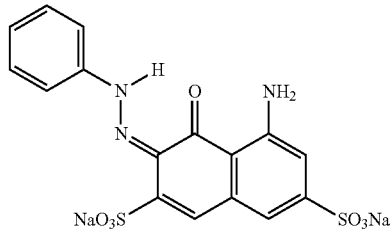

(D)
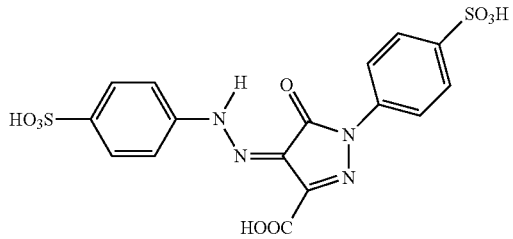

Compound (A) is known as Acid Black 1, Duramine Black 10B and Black-Blue 10B.

Compound (B) is known as Acid Orange 7 and Duramine Orange II.

Compound (C) is known as Acid Red 33 and D&C Red 33.

Compound (D) is known as Acid Yellow 23, Acid Tartrazine and Eurogran tartrazine.

Examples of suitable dyes include those of the following group, (2):

(E)
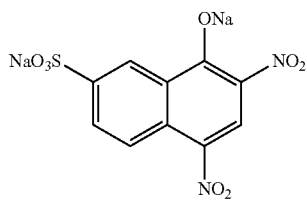

(F)
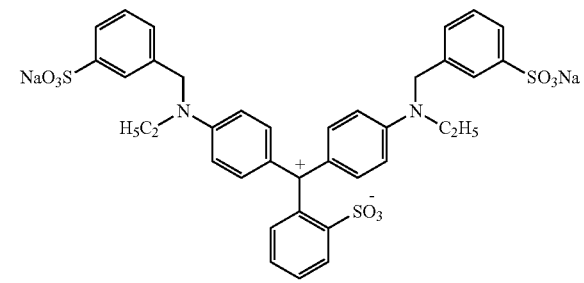

-continued

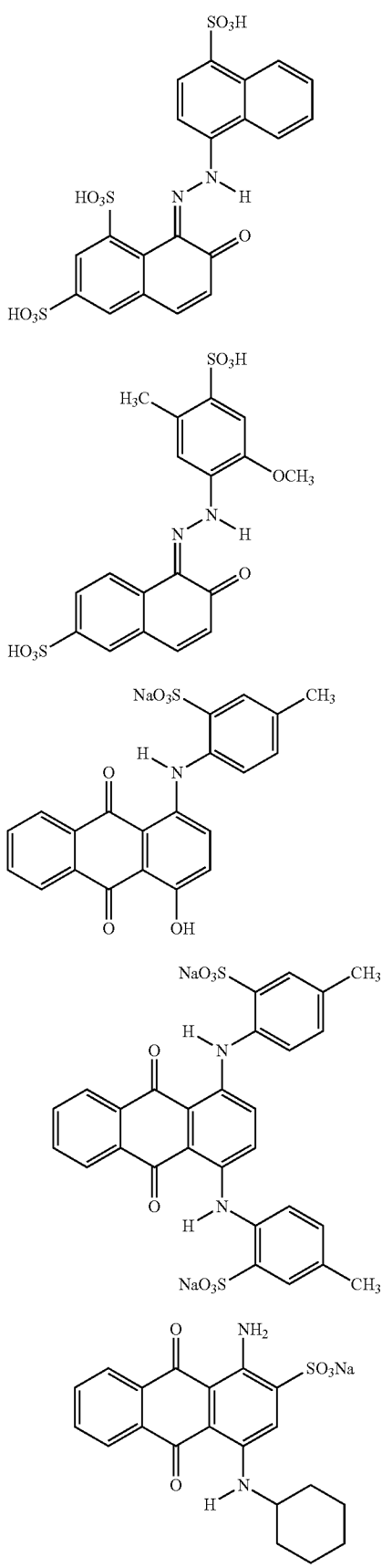

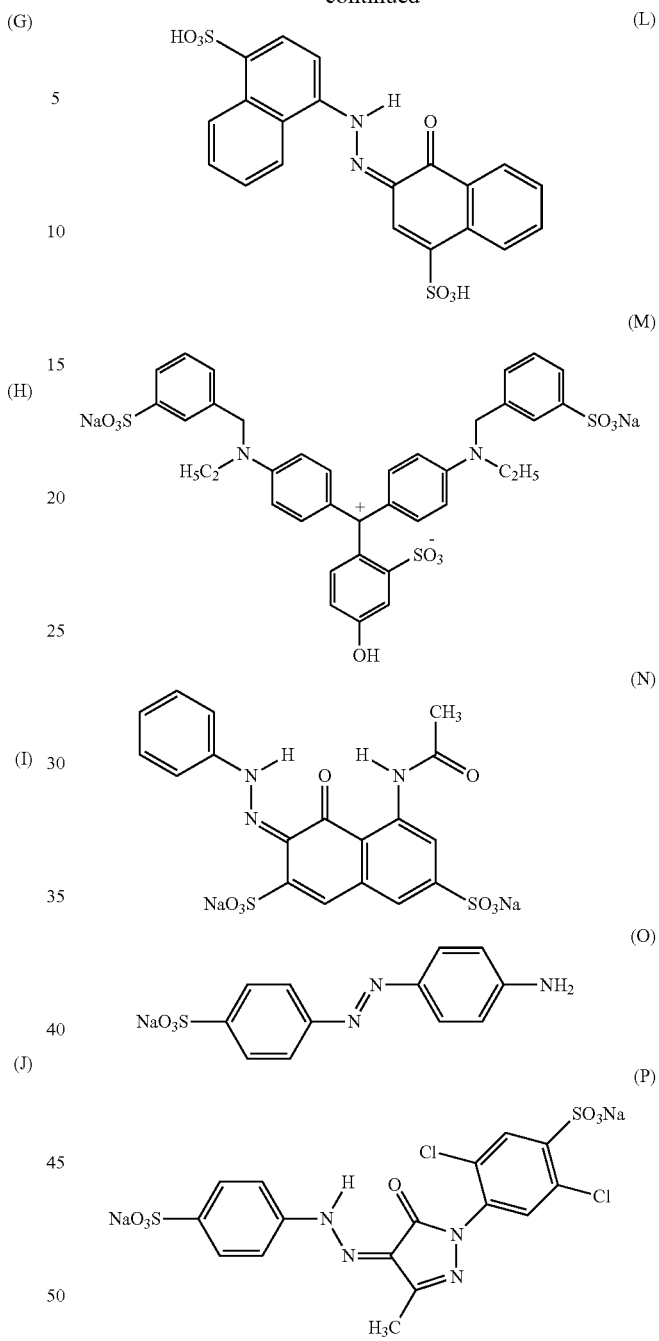

Compound (E) is known as Acid Yellow 1, Ext D&C Yellow 1 and Naphthol Yellow S.

Compound (F) is known as Acid Blue 9, Duracol Brilliant Blue FCF E133, Food Blue 2 and FD&C Blue 1.

Compound (G) is known as Acid Red 18, Duracol Ponceau 4R E124, Eurocert Ponceau 4R and Food Red 18.

Compound (H) is known as Food Red 17 and FD&C Red 40.

Compound (I) is known as Acid Violet 43 and Ext. D&C Violet 2.

Compound (J) is known as Acid Green 25 and D&C Green 5.

Compound (K) is known as Acid Blue 62, Acid Brilliant Blue R and Duramine Blue R.

Compound (L) is known as Acid Red 14, Food Red 3 and Duracol Carmoisine.

Compound (M) is known as Food Green 3 and D&C Green 3.

Compound (N) is known as Acid Red 1 and Lissamine Red 2G.

Compound (O) is known as Direct Orange 39 and Solar Orange 2GL.

Compound (P) is known as Acid Yellow 17, Duramine Yellow 2G and Acrolan Yellow 2G.

Examples of suitable dyes include those of the following group, (3):

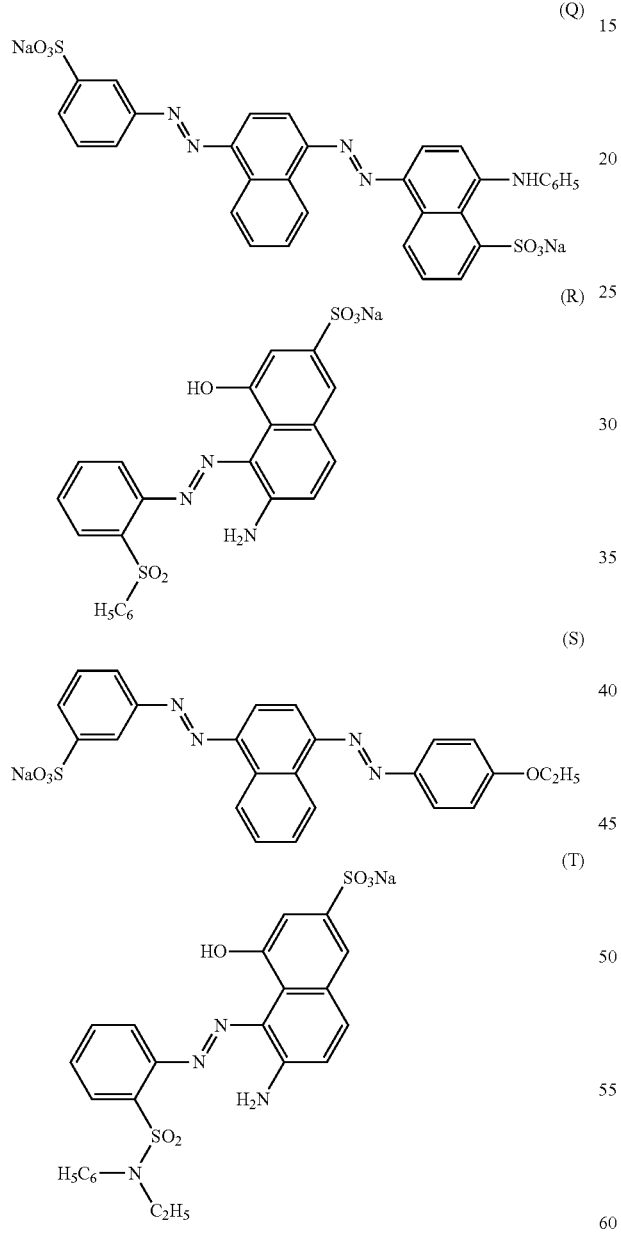

Compound (Q) is known as Acid Blue 113 and Telon Navy AMF.

Compound (R) is known as Acid Red 42, Telon Red BN and Acidol Red 2BE-NR.

Compound (S) is known as Acid Orange 127 and Nylosan Orange N-RL.

Compound (T) is known as Acid Red 57 and Duramine Red 3G.

Examples of suitable dyes include those of the following group, (4):

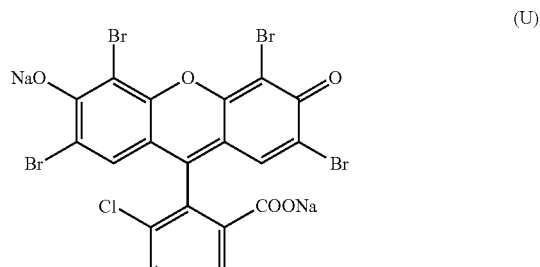

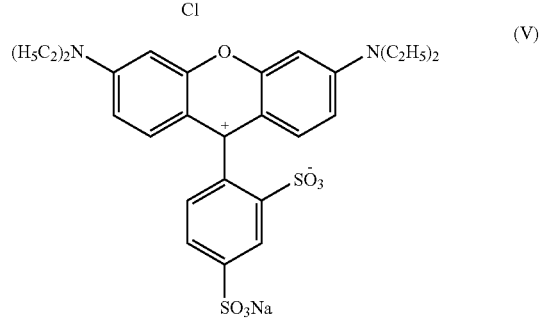

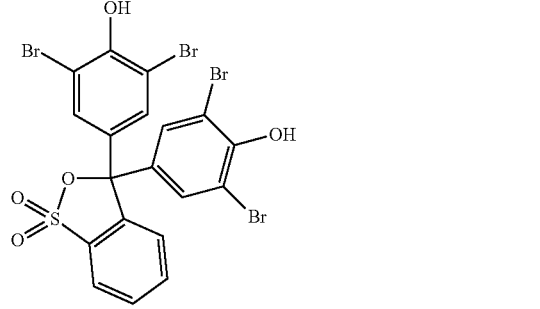

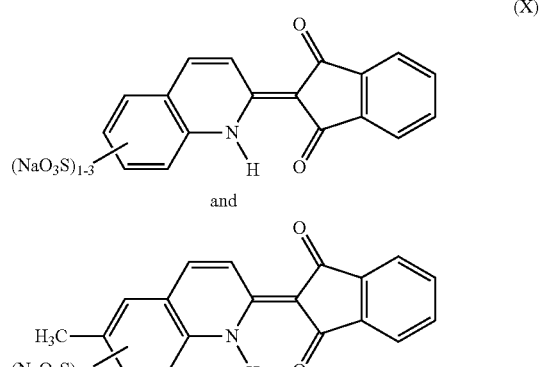

Compound (U) is known as Acid Red 92 and D&C Red 28.

Compound (V) is known as Acid Red 52, Acid Rhodamine B and Nylosan Rhodamine B.

Compound (W) is known as Tetrabromophenol Blue.

Compound (X) is known as Acid Yellow 3 and D&C Yellow 10.

The names given above represent a non-exhaustive list and compounds having the structures shown may also be known by other names. Although the above mentioned trade names may change, the skilled person would be able to consult the Colour Index International to identify the dye compound and find a current manufacturer.

The colouring composition contacted with the hair in step (i) preferably comprises a dye compound selected from those in group (1), group (2), group (3) or group (4).

The colouring composition comprises a dye compound selected from those in group (1), group (2) or group (3).

More preferably the colouring composition comprises a dye compound selected from those in group (1) or group (2).

Most preferably the colouring composition comprises a dye compound selected from those in group (1).

The colouring compositions used in step (i) of the method of the present invention may include a mixture of two or more dye compounds. Mixtures of dyes may be combined in a specific ratio to achieve a desired colour or other visual effect.

The colouring composition preferably comprises at least 0.0001 wt % of the dye compound. Preferably it comprises at least 0.001 wt %, more preferably at least 0.01 wt %, suitably at least 0.05 wt %, preferably at least 0.1 wt %, for example at least 0.5 wt %. The colouring composition suitably comprises up to 40 wt % of the dye compound, preferably up to 30 wt %, more preferably up to 25 wt %, suitably up to 20 wt %, preferably up to 15 wt %, more preferably up to 12 wt %, for example up to 10 wt %.

The amount of dye included in the colouring composition may vary significantly depending on the strength of colour it is desired to achieve.

The above amounts refer to the total amount of all dye compounds present in the colouring composition (for application as a single composition). Commonly mixtures of two or more dyes will be included, the relative amount being dependent on the desired shade required and the preparation of such mixtures will be readily understood by those skilled in the art.

The colouring composition preferably comprises a swelling agent. This is suitably present in an amount of from 0.01 to 50 wt %, preferably from 0.1 to 20 wt %. A preferred swelling agent is urea.

The colouring composition preferably comprises at least 0.1 wt % urea. Without being bound by theory it is believed that urea helps to solubilise the dye compounds in the composition and/or denatures keratinous proteins found in hair (and animal fibres) and increases the rate of reaction with the fibre substrate. In addition urea helps to swell the hair.

Urea may suitably be present in the colouring composition in an amount of at least 0.5 wt %, preferably at least 1 wt %, suitably at least 2 wt %, preferably at least 3% wt, for example at least 4 wt %.

Urea may suitably be present in an amount up to 40 wt % of the colouring composition, preferably up to 30 wt %, more preferably up to 25 wt %, suitably up to 20 wt %, preferably up to 15 wt %, for example up to 12 wt %.

The colouring composition preferably comprises less than 0.1 wt % thiourea. Preferably the colouring composition does not comprise thiourea.

The colouring composition preferably comprises a thiol. Suitable thiols include thioglycolic acid, thiolactic acid, dihydrolipoate, thioglycerol, mercaptopropionic acid, cysteine, N-substituted cysteines, cysteamines, N-substituted cysteamines, thioethanol, thiosulfate, sulfide anion, 1-thiopropane 3-sulfonate, and salts and/or esters thereof.

Preferably the composition of the present invention comprises at least 0.25 wt % thiol, preferably at least 0.4 wt %, more preferably at least 0.5 wt %, preferably at least 0.6 wt %, suitably at least 0.7 wt %, for example at least 0.8 wt %.

The composition may comprise up to 10 wt % thiol, preferably up to 7.5 wt %, more preferably up to 5 wt %, suitably up to 2.5 wt %, preferably up to 2 wt %, more preferably up to 1.75 wt %, for example 1.5 wt %.

The composition of the present invention may comprise a mixture of thiols. In such embodiments the above amounts refer to all thiols present.

An especially preferred thiol is thioglycolic acid. Thioglycolic acid may be provided as the free acid or as an ester or a salt.

Preferred salts include ammonium, substituted ammonium, alkali metal and alkaline earth metal salts.

Suitable esters include $C_1$ to $C_4$ esters and glycerol esters. The glycerol ester (glycerol trithioglycolate) is one useful ester.

In some preferred embodiments thioglycolic acid may be added to the composition as the free acid but may be present as a salt due to the pH of the composition.

Preferably thioglycolic acid or a salt thereof is the only thiol present in the composition.

Preferably the composition comprises from 0.1 to 2.5 wt % thioglycolic acid or a salt thereof, preferably from 0.5 to 1.5 wt %.

The colour composition contacted with the hair in step (i) of the method of the present invention may comprise one or more further ingredients for example colourants, fragrances, emollients, thickeners, pH adjusting agents, surfactants and chelating agents. The selection of such components is within the competence of the skilled person in the art.

The colouring composition is preferably an aqueous composition. Suitably it comprises at least 50 wt % water, preferably at least 70 wt % water, more preferably at least 80 wt %. The colouring composition may also comprise one or more water miscible cosolvents. One preferred cosolvent is glycerol. This is suitably present in an amount of from 0.1 to 20 wt %, preferably from 0.5 to 10 wt %, for example from 1 to 3 wt %.

Preferably the colouring composition has a pH of from 8 to 11, preferably from 9 to 10.5.

In some embodiments the colouring composition may be prepared immediately prior to application to the hair, for example from two or more precursor compositions. Compositions of this type are known to the person skilled in the art and allow components that may interact with each other to be stored separately to increase the shelf life of the product. Typically the colouring compositions may be prepared from a first precursor composition comprising a dye compound and a second precursor composition comprising a thiol.

It has been found that improved dyeing can be achieved if the composition is contacted with the hair at a temperature above ambient temperature.

Thus in preferred embodiments step (i) of the method of the present invention comprises contacting the material with a colouring composition at a temperature of at least 30° C., suitably at a temperature of between 30° C. and 50° C., preferably between 35° C. and 45° C.

The colouring composition is preferably contacted with the material for a period of at least 1 minute, preferably at least 2 minutes, more preferably at least 5 minutes, for example at least 10 minutes, or at least 15 minutes.

It may be contacted with the material for a period of up to 4 hours, suitably up to 3 hours, preferably up to 2 hours, for example up to 1.5 hours. A contact time of 30 to 60 minutes is especially preferred.

The colouring composition may be applied to the hair by any suitable means. Such methods are well known to those skilled in the art and include for example brushing the composition (which may suitably be in the form of a paste) onto the hair.

The compositions may be suitably applied to hair at a liquor ratio of from 10:1 to 0.5:1, preferably from 5:1 to 1:1, for example from 3:1 to 2:1.

The compositions may suitably be rinsed from the hair with warm water.

Step (ii) of the method of the present invention involves contacting the material with a composition comprising a quaternary ammonium salt.

Suitable quaternary ammonium salts include those compounds containing a single quaternary ammonium cationic centre and compounds including multiple quaternary ammonium cationic centres, for example polymeric compounds.

Preferred quaternary ammonium salts are compounds of the formula I

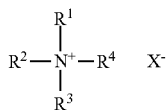

wherein each of $R^1$, $R^2$, $R^3$ and $R^4$ is selected from an optionally substituted alkyl or alkenyl group and $X^-$ is a suitable anion.

Preferably each of $R^1$, $R^2$, $R^3$ and $R^4$ is independently selected from an unsubstituted alkyl and alkenyl group. Preferably each of $R^1$, $R^2$, $R^3$ and $R^4$ is independently selected from an unsubstituted alkyl or alkenyl group, preferably an alkyl or alkenyl group having 1 to 36 carbon atoms.

$R^1$ is preferably an unsubstituted alkyl or alkenyl group having from 1 to 36 carbon atoms, preferably from 4 to 32 carbon atoms, more preferably from 8 to 30 carbon atoms, preferably from 10 to 28 carbon atoms, preferably from 12 to 26 carbon atoms, suitably from 14 to 24 carbon atoms. Preferably $R^1$ is an unsubstituted alkyl group.

In especially preferred embodiments $R^1$ is selected from a cetyl group ($C_{16}$ alkyl), a behenyl group ($C_{22}$ alkyl), a stearyl group ($C_{18}$ alkyl) and mixtures thereof.

In some embodiments $R^2$ may be a $C_6$ to $C_{36}$ alkyl group, preferably a $C_8$ to $C_{30}$ alkyl group, preferably a $C_{10}$ to $C_{28}$ alkyl group, for example a $C_{14}$ to $C_{24}$ alkyl group.

In preferred embodiments $R^2$ is $C_1$ to $C_4$ alkyl group. More preferably $R^2$ is selected from methyl and ethyl. Most preferably $R^2$ is a methyl group.

In some embodiments $R^3$ may be a $C_6$ to $C_{36}$ alkyl group, preferably a $C_8$ to $C_{30}$ alkyl group, preferably a $C_{10}$ to $C_{28}$ alkyl group, for example a $C_{14}$ to $C_{24}$ alkyl group.

In preferred embodiments $R^3$ is $C_1$ to $C_4$ alkyl group. More preferably $R^3$ is selected from methyl and ethyl. Most preferably $R^3$ is a methyl group.

In some embodiments $R^4$ may be a $C_6$ to $C_{36}$ alkyl group, preferably a $C_8$ to $C_{30}$ alkyl group, preferably a $C_{10}$ to $C_{28}$ alkyl group, for example a $C_{14}$ to $C_{24}$ alkyl group.

In preferred embodiments $R^4$ is $C_1$ to $C_4$ alkyl group. More preferably $R^4$ is selected from methyl and ethyl. Most preferably $R^4$ is a methyl group.

In especially preferred embodiments $R^2$, $R^3$ and $R^4$ are all hydrogen and $R^1$ contains one or more $C_{16}$ to $C_{22}$ alkyl groups.

$X^-$ may be any suitable anion. $X^-$ is preferably a halide ion. Preferred halides are chloride and bromide ions. Most preferably $X^-$ is a chloride ion.

In some especially preferred embodiments step (ii) of the method of the present invention comprises contacting the material with a composition comprising a quaternary ammonium salt selected from cetyltrimethyl ammonium chloride, stearyltrimethyl ammonium chloride, behenyltrimethyl ammonium chloride and mixtures thereof.

In some embodiments the composition contacted with the material in step (ii) of the method of the present invention may comprise a quaternary ammonium salt having multiple quaternary ammonium centre. Suitable quaternary ammonium compounds include polycationic polymers containing multiple quaternary ammonium centres referred to on the INCI list as "Polyquaternium" compounds. The composition of the present invention may include any polyquaternium compound listed on the INCI list. Other suitable compounds include polycationic polyamine compounds used in the textile/paper industry for improving wash fastness of dyes or dyeability. Examples of such compounds include, but are not limited to, polymers made by condensing dicyandiimide and diethylene triamine.

The composition contacted with the material in step (ii) of the method of the present invention preferably comprises at least 0.1 wt % of one or more quaternary ammonium salts, preferably at least 0.5 wt %, more preferably at least 1 wt %, suitably at least 2 wt %, more preferably at least 3 wt %, for example at least 4 wt %.

The composition contacted with the material in step (ii) of the method of the present invention may comprise up to 40 wt % of one or more quaternary ammonium salts, preferably up to 30 wt %, suitably up to 20 wt %, more preferably up to 10 wt %, preferably up to 8 wt %, suitably up to 6 wt %.

The composition used in step (ii) may comprise a mixture of quaternary ammonium salts. In such embodiments the above amounts refer to as such the total of all quaternary ammonium salts present in the composition.

The skilled person will appreciate that commercial sources of quaternary ammonium salts often contain large amounts of impurities, for example unreacted starting materials or byproducts, and diluents or carriers. For the avoidance of doubt the above amounts refer to the actual amount of quaternary ammonium salt present in the composition.

The composition contacted with the material in step (ii) is preferably an aqueous composition. In some embodiments the composition comprises at least 50 wt % water, preferably at least 60 wt %, more preferably at least 70 wt %.

Suitably water accounts for at least 50 wt % of all solvents present in the composition, preferably at least 70 wt %, for example at least 90 wt %.

The composition contacted with the material in step (ii) is preferably an acidic composition. Suitably it has a pH of from 1 to 6, preferably from 2 to 5, more preferably from 3 to 4.

The composition may comprise one or more cosolvents, especially preferred cosolvents are alcohols especially fatty alcohols, an especially preferred cosolvent is cetearyl alcohol. This may be present in an amount of from 0.1 to 20 wt %, suitably in an amount of from 1 to 10 wt %, for example from 3 to 8 wt %.

The composition may suitably include an emollient. This may be present in an amount of from 0.1 to 10 wt %, for example from 0.5 to 5 wt %. Suitable emollients will be known to the person skilled in the art. One preferred emollient is shea butter.

The composition contacted with the material in step (ii) of the method of the invention may suitably comprise further ingredients for example selected from solvents, preservatives, thickeners, perfumes, pH adjustment agents and surfactants. Suitable components of this type will be known to the person skilled in the art.

Preferably the composition contacted with the material in step (ii) does not contain a pigment, dye or other colourant.

The composition applied to the hair in step (ii) may be regarded as a conditioning composition. It suitably has the consistency of a typical conditioning composition of the type generally known and may be applied to the hair in a similar manner. The composition may suitably be massaged or rubbed into the hair or brushed onto the hair.

Suitably the composition is contacted with the material in step (ii) of the method of the present invention for a period of from 0.1 to 60 minutes, preferably 0.5 to 30 minutes, suitably 1 to 20 minutes, preferably 2 to 10 minutes.

Suitably the composition is rinsed from the hair with water, preferably warm water.

It has been found that when a composition comprising a quaternary ammonium salt is contacted with the hair as defined in step (ii) of the method of the present invention a significant reduction in "bleeding" of colour from the dyed hair is seen compared to when a typical commercially available conditioning composition of the prior art is used. Such compositions typically contain silicone compounds as the major conditioning agent.

Preferably the composition contacted with the hair in step (ii) comprises less than 2 wt % silicone compounds, preferably less than 1 wt %, more preferably less than 0.5 wt %, most preferably less than 0.1 wt %, especially less than 0.01 wt %.

In preferred embodiments following step (i) of the method of the present invention the material is rinsed with water, suitably warm water. After this rinsing step it is preferable to contact the material, most suitably hair, with an oxidising composition. This oxidising composition is then rinsed from the hair, suitably with warm water prior to step (ii).

Thus in especially preferred embodiments the method of the first aspect of the present invention comprises the steps of:
(a) contacting the material with colouring composition comprising a dye compound;
(b) rinsing the material;
(c) contacting the material with an oxidising composition;
(d) rinsing the material; and
(e) contacting the material with a composition comprising a quaternary ammonium salt.

As mentioned above the material is preferably hair, especially human hair.

The oxidising composition contacted with the hair in step (c) preferably comprises a source of peroxide. Preferably it comprises hydrogen peroxide. The oxidising composition preferably comprises from 0.1 to 10 wt %, preferably 0.25 to 2.5 wt %, for example 0.5 to 1.5 wt % hydrogen peroxide.

The oxidising composition is preferably an aqueous composition. It is preferably a shampoo composition. By this we mean that in addition to a source of peroxide, the composition suitably comprises components typically found in a commercial shampoo formulation. Thus the oxidising composition may comprise a mixture of surfactants, suitably including anionic, cationic and non-ionic surfactants; along with other ingredients for example thickeners, solvents, colourants, fragrances, preservatives, antioxidants, chelating agents, emollients and biocides.

The oxidising composition is preferably acidic. It may comprise any suitable acid. Preferred acids include acetic acid and citric acid. Preferably the oxidising composition has a pH of from 3 to 6, preferably from 3.5 to 4.5.

The oxidising composition is suitably applied to the hair in the manner of a typical shampoo composition. It may suitably be massaged or rubbed into the hair or brushed onto the hair.

Suitably the oxidising composition is allowed to remain on the hair for a period of 0.1 to 60, preferably 1 to 20, more preferably 2 to 10 minutes.

The method preferably includes a further step (f) after step (e) of rinsing the material. Suitably the material is rinsed with water. However embodiments in which the composition applied in step (e) is allowed to remain on the hair are also within the scope of the invention.

According to a second aspect of the present invention there is provided an anti-bleed composition comprising from 1 to 10 wt % of a mixture of quaternary ammonium salts selected from cetyltrimethyl ammonium chloride, stearyltrimethyl ammonium chloride, behenyltrimethyl ammonium chloride and mixtures thereof.

According to a third aspect of the present invention there is provided a packaged hair colouring product comprising a hair colouring composition or a precursor thereof and a composition comprising a quaternary ammonium compound.

The packaged hair colouring product may comprise a first hair colouring precursor composition comprising a dye compound, a second hair colouring precursor composition comprising a thiol and a composition comprising a quaternary ammonium compound.

Preferably the packaged hair colouring composition further comprises an oxidising composition.

According to a fourth aspect of the present invention there is provided the use of a composition comprising a quaternary ammonium salt to reduce bleeding of colour from dyed hair.

By bleeding of colour we mean to refer to colour migrating from the hair into or onto another medium which the hair comes into contact with.

The invention will now be further defined with reference to the following non limiting examples.

Preferred features of the second, third and fourth aspect are as defined in relation to the first aspect.

EXAMPLE

A hair colouring composition was prepared by mixing the following two part compositions in a 1:1 ratio:

TABLE 1

| Part 1 - Colour Tube | | Part 2 - Colour gel | |
|---|---|---|---|
| Acid Black 1 | 1.5925% | Water | 84.3% |
| Acid Orange 7 | 1.25% | Urea | 10% |
| Acid Red 33 | 0.265% | Aminomethyl propanol* | 2.7% |
| Glycerol | 4% | Thioglycolic acid | 2% |
| Sodium laureth sulphate | 2% | Hydroxyethylcellulose | 1% |
| Hydroxy-ethylcellulose | 2% | *pH adjusted to 9.5 with aminomethyl propanol | |
| Perfume | 0.05% | | |
| Water | 88.8425% | | |
| pH adjusted to 9.5 with sodium hydroxide | | | |

This formulation will give a Neutral 4 colour when applied to bleached light brown hair.

The mixture was brushed onto hair tresses and left for 30 to 60 minutes as required, and then rinsed from the hair with warm water.

An acidic shampoo composition containing 1 wt % hydrogen peroxide and having a pH of 4 was massaged into the hair and left for 5 minutes. The hair was then rinsed with warm water.

A conditioning composition was then massaged into the hair and left for 5 minutes. The hair was then rinsed with warm water and dried.

The dried hair tresses were submerged in deionised water at room temperature for 30 minutes. They were then removed and placed onto white tissue paper whilst soaking wet and the hair was allowed to dry naturally.

The following conditioning agents were tested:
1. No conditioner after-treatment
2. Elvive Nutri-Gloss Shine Conditioner
3. Herbal Essences dazzling shine conditioner
4. Head & Shoulders Classic Clean conditioner
5. Pantene Pro-V Classic Care conditioner
6. Tresemmé Luxurious moisture conditioner
7. A conditioning agent of the invention having the formulation shown in table 2.

Figure 2:
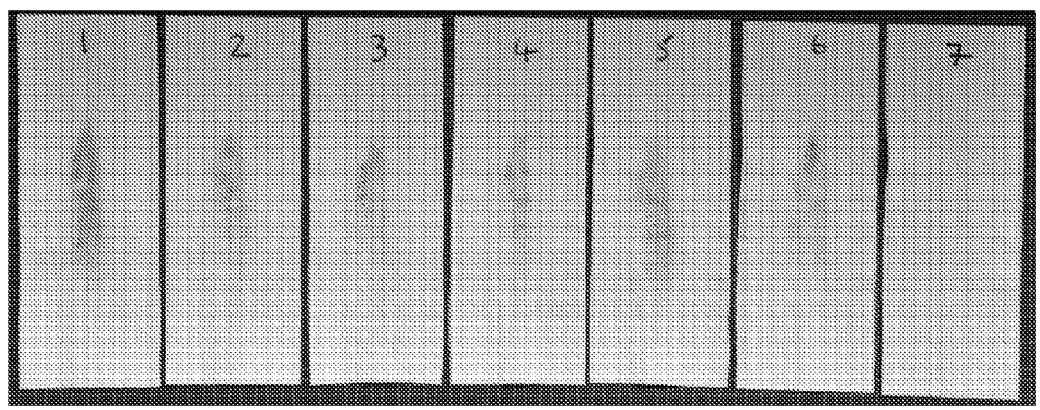

FIG. 1 shows a photograph of the water jars in which the hair tresses were submerged and FIG. 2 shows a photograph of the tissue paper on which the hair tresses were dried. These clearly show that the composition of the invention significantly reduces bleeding from dyed hair.

| COMPONENT | [wt %] |
|---|---|
| Cetyl trimethyl ammonium chloride | 2.25 |
| Cetearyl alcohol | 5.80 |
| Behenyl trimethyl ammonium chloride | 2.40 |
| Shea butter | 2.47 |
| Stearyl trimethyl ammonium chloride | 0.425 |
| Silcpro | 0.50 |
| Alpaflor gigawhite extract | 0.50 |
| Hydroxyethylcellulose | 0.50 |
| DMDM hydantoin | 0.25 |
| Perfume | 0.25 |
| Citric acid | 0.05 |
| Deionised water | to 100% |

The amounts given in the table above refer to the active amount of each component present.

Cetyl trimethyl ammonium chloride was supplied as a 30% active composition.

Behenyl trimethyl ammonium chloride was supplied as an 80% active composition.

Stearyl trimethyl ammonium chloride was supplied as an 85% active composition.

Silcpro contains aqua, hydrolyzed silk, butylene, glycol, methylparaben, and propylparaben.

Alpaflor gigawhite extract contains a mixture of plant extracts.

The invention claimed is:

1. A method of treating a material, the method comprising the steps of:
   a) contacting the material with colouring composition comprising a water soluble dye compound containing sulfonate and/or carboxylate groups and that includes a chromophore and a thiol selected from thioglycolic acid, thiolactic acid, dihydrolipoate, thioglycerol, mercaptopropionic acid, cysteine, N-substituted cysteines, cysteamines, N-substituted cysteamines, thioethanol, thiosulfate, sulfide anion, 1-thiopropane 3-sulfonate, and salts and/or esters thereof;
   b) rinsing the material;
   c) contacting the material with an oxidising composition;
   d) rinsing the material; and
   e) contacting the material with a composition comprising a quaternary ammonium salt.

2. A method according to claim 1 wherein the material is hair.

3. A method according to claim 1 wherein the colouring composition comprises a swelling agent.

4. A method according to claim 1 wherein the colouring composition has a pH of from 8 to 11.

5. A method according to claim 1 wherein the quaternary ammonium salt contacted with the material in step (e) is selected from compounds containing a single quaternary ammonium cationic centre and compounds including multiple quaternary ammonium cationic centres.

6. A method according to claim 5 wherein the quaternary ammonium salt is selected from compounds of formula

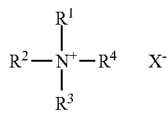

wherein R1 is an unsubstituted alkyl or alkenyl group having from 4 to 32 carbon atoms; R2 is C1 to C4 alkyl group; R3 is C1 to C4 alkyl group; R4 is C1 to C4 alkyl group; and X$^-$ is a halide ion.

7. A method according to claim 6 wherein the quaternary ammonium salt is selected from cetyltrimethyl ammonium chloride, stearyltrimethyl ammonium chloride, behenyltrimethyl ammonium chloride and mixtures thereof.

8. A method according to claim 1 wherein the composition contacted with the material in step (e) is an acidic composition.

9. A method according to claim 1 wherein the oxidising composition contacted with the hair in step (c) comprises hydrogen peroxide.

10. A method according to claim 9 wherein the oxidising composition comprises from 0.25 to 2.5 wt % hydrogen peroxide.

11. A method according to claim 1 wherein the oxidising composition has a pH of from 3 to 6.

* * * * *